United States Patent
Bianchi et al.

(10) Patent No.: US 9,908,947 B2
(45) Date of Patent: *Mar. 6, 2018

(54) BIOTECHNOLOGICAL SULPHATED CHONDROITIN SULPHATE AT POSITION 4 OR 6 ON THE SAME POLYSACCHARIDE CHAIN, AND PROCESS FOR THE PREPARATION THEREOF

(71) Applicant: Gnosis S.p.A., Milan (IT)

(72) Inventors: Davide Bianchi, Desio (IT); Marco Valetti, Desio (IT); Paola Bazza, Desio (IT); Niccolo Miraglia, Desio (IT); Ermanno Valoti, Dalmine (IT)

(73) Assignee: Gnosis S.p.A., Milan (IT)

( * ) Notice: Subject to any disclaimer, the term of this patent is extended or adjusted under 35 U.S.C. 154(b) by 42 days.

This patent is subject to a terminal disclaimer.

(21) Appl. No.: 14/977,119

(22) Filed: Dec. 21, 2015

(65) Prior Publication Data
US 2016/0108139 A1 Apr. 21, 2016

Related U.S. Application Data

(62) Division of application No. 14/115,184, filed as application No. PCT/EP2012/058654 on May 10, 2012, now abandoned.

(30) Foreign Application Priority Data

May 12, 2011 (IT) .............................. MI2011A0829
Feb. 2, 2012 (IT) .............................. MI2012A0136

(51) Int. Cl.
C08B 37/00 (2006.01)
A61K 31/737 (2006.01)
C08L 5/08 (2006.01)

(52) U.S. Cl.
CPC ........ *C08B 37/0069* (2013.01); *A61K 31/737* (2013.01); *C08L 5/08* (2013.01)

(58) Field of Classification Search
None
See application file for complete search history.

(56) References Cited

U.S. PATENT DOCUMENTS

| 3,405,120 | A | 10/1968 | Kawano et al. |
| 4,704,356 | A | 11/1987 | Thonar |
| 6,777,398 | B2* | 8/2004 | Zoppetti ............. C08B 37/0069 |
| | | | 514/54 |

FOREIGN PATENT DOCUMENTS

| EP | 1304388 | 4/2003 |
| WO | 2009/149155 | 12/2009 |
| WO | 2012/062917 | 5/2012 |

OTHER PUBLICATIONS

Bedini, Chem. Eur. J. 2012, 18, 2123-2130, published Jan. 9, 2012.*
Bedini, E., et al., A Microbiological-Chemical Strategy . . . , Angew. Chem. Int. Ed., vol. 50, pp. 6160-6163, 2011.
D'Arcy, s., et al., Preliminary Investigation Into the Purification . . . , Carbohydrate Research, vol. 255, pp. 41-59, 1994.
Fujikawa, S., Enzymatic Synthesis of Chondroitin 4-Sulfate with Well-Defined Structure, Biomolecules 2005, 6, 2935-2942.
International Search Report issued in counterpart PCT Application No. PCT/EP2012/058654.
Khan, R., et al., Selective Acetylation Reactions of Hyaluronic . . . , Carbohydrate Reasearch, vol. 306, pp. 137-146, 1998.
Volpi, N., et al., Analytical Aspects of Pharmaceutical . . . , Journal of Pharma. Sci., vol. 96, No. 12, 2007.
Volpi, N., et al., Influence of Charge Density, Sulfate Group . . . , Biomaterials, vol. 23, pp. 3015-3022, 2002.
Written Opinion of International Searching Authority issued in counterpart PCT Application No. PCT/EP2012/058654.

* cited by examiner

*Primary Examiner* — Layla D Berry
(74) *Attorney, Agent, or Firm* — Amin Talati Upadhye LLP; George M. Carrera, Jr.; Yichen Cao

(57) ABSTRACT

The present invention discloses a process for the production of chondroitin sulphate with an average molecular weight (Mw) of 10-30 kDa by chemical sulphation starting from an unsulphated chondroitin backbone, obtained in turn by acid hydrolysis of capsular polysaccharide K4 made directly from *E. coli* strain O5:K4:H4, or directly produced from a genetically modified strain of *E. coli*. Sulphation of the N-acetyl-D-galactosamine residue at position 4 or 6 takes place simultaneously in the same polysaccharide chain, simulating the sulphation pattern observed in natural chondroitin sulphate, unlike the sulphation obtained with the synthesis methods described to date.

13 Claims, 3 Drawing Sheets

Figure 1:
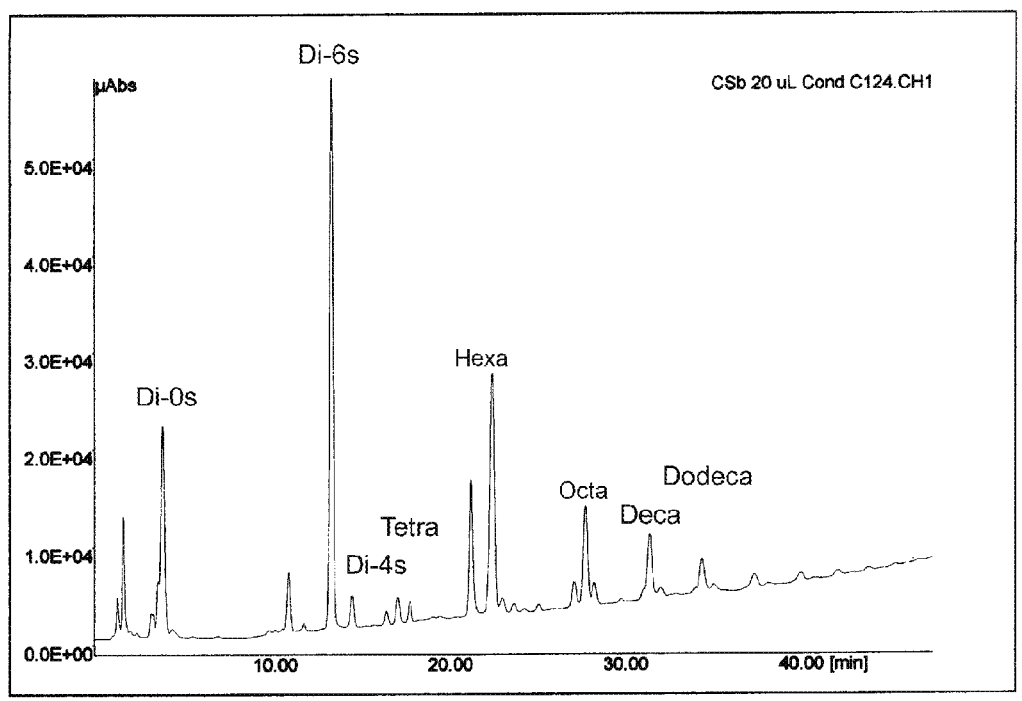

BIOTECHNOLOGICAL SULPHATED CHONDROITIN SULPHATE AT POSITION 4 OR 6 ON THE SAME POLYSACCHARIDE CHAIN, AND PROCESS FOR THE PREPARATION THEREOF

This application is a divisional of U.S. application. Ser. No. 14/115,184, filed Dec. 4, 2013, which is the U.S. National Stage application under § 371 of PCT/EP2012/058654, filed on May 10, 2012, which claims priority from Italian Application Nos. MI2012A000136, filed on Feb. 2, 2012, and MI2011A000829, filed on May 12, 2011, each of which is hereby incorporated by reference herein.

TECHNICAL FIELD OF INVENTION

The present invention relates to a method for the production of chondroitin sulphate by chemical sulphation starting from an unsulphated chondroitin backbone. The process according to the invention allows simultaneous sulphation, within the same polysaccharide chain, of position 4 or position 6 of the N-acetyl-D-galactosamine residue. The chondroitin sulphate thus obtained presents the same sulphation pattern as observed in natural chondroitin sulphate, unlike that obtained with the synthesis methods described so far.

The invention also relates to a chondroitin sulphate which has an average molecular weight determined by SEC (Mw) of 4-9 kDa, and a distribution of mono-sulphated groups ranging from 90% 4-sulphate and 10% 6-sulphate to 10% 4-sulphate and 90% 6-sulphate.

TECHNICAL BACKGROUND

Chondroitin sulphate (CS) is a complex natural polysaccharide belonging to the glycosaminoglycan (GAG) class, consisting of disaccharide sequences formed by residues of glucuronic acid (GlcA) and N-acetyl-D-galactosamine (GalNAc) sulphated in different positions and bonded by beta 1-3 bonds.

CS is present in animal tissues, with structural and physiological functions. Depending on its origin, CS mainly consists of variable percentages of two types of disaccharide unit monosulphated at position 4 or position 6 of GalNAc (disaccharides A and C respectively). However, disaccharides in which the sulphate groups are present in different numbers and different positions may be present in various percentages in the polysaccharide chains. The CS backbone also contains unsulphated disaccharide, generally in small quantities. Disulphated disaccharides having two sulphate groups bonded through the oxygen atom in various positions, such as position 2 of GlcA and 6 of GalNAc (disaccharide D), position 2 of GlcA and 4 of GalNac, or positions 4 and 6 of GalNAc (disaccharide E), can be present in the CS backbone in variable percentages, depending on the specific animal sources (Volpi N. J Pharm Pharmacol 61, 1271, 2009. Volpi N. J Pharm Sci 96, 3168, 2007. Volpi N. Curr Pharm Des 12, 639, 2006).

The repeating disaccharide unit found in CS has the following chemical formula:

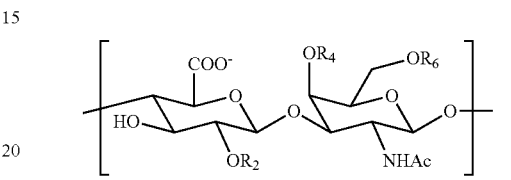

wherein $R_2$, $R_4$ and $R_6$ are independently H or $SO_3^-$.

The negative charges of the carboxylate and sulphate groups in the repeating disaccharide unit are neutralised by sodium ions.

The meanings of the acronyms most commonly used to identify the variously sulphated disaccharides are set out below:

Di-0S (R2=H; R4=H; R6=H)
Di-6S (C) (R2=H; R4=H; R6=SO3-)
Di-4S (A) (R2=H; R4=SO3-; R6=H)
Di-4,6diS (E) (R2=H; R4=SO3-; R6=SO3-)
Di-2,6diS (D) (R2=SO3-; R4=H; R6=SO3-)
Di-2,4diS (B) (R2=SO3-; R4=SO3-; R6=H)
Di-2,4,6triS (R2=SO3-; R4=SO3-; R6=SO3-)

Samples of CS originating from different animal sources are also characterised by different molecular weights and charge densities, this latter parameter being directly correlated with the specific sulphated groups.

Table 1 shows the main disaccharides found in natural CS extracted from cartilage and other tissues of various animal species:

TABLE 1

|  | Bovine CS | Porcine CS | Chicken CS | Shark CS | Skate CS | Squid CS |
|---|---|---|---|---|---|---|
| Mn (kDa) | 12-17 | 9-14 | 8-13 | 25-40 | 27-34 | 60-80 |
| Mw (kDa) | 20-26 | 14-20 | 16-21 | 50-70 | 50-70 | 80-120 |
| Polydispersity index | 1.8-2.2 | 1.4-1.8 | 1.6-2.0 | 1.0-2.0 | 1.2-2.5 | 0.8-1.3 |
| Di-0S | 6 | 6 | 8 | 3 | 3 | 13 |
| Di-6S | 33 | 14 | 20 | 44 | 39 | 15 |
| Di-4S | 61 | 80 | 72 | 32 | 43 | 50 |
| Di-2,6diS | ND | ND | ND | 18 | 13 | 0 |
| Di-4,6diS | ND | ND | ND | 2 | 1 | 22 |
| Di-2,4diS | ND | ND | ND | 1 | 1 | 0 |
| Charge density | 0.90-0.96 | 0.92-0.96 | 0.90-0.94 | 1.15-1.25 | 1.08-1.20 | 1.00-1.20 |
| Ratio 4S/6S | 1.50-2.00 | 4.50-7.00 | 3.00-4.00 | 0.45-0.90 | 1.00-1.40 | 2.50-4.00 |

Mn = number average molecular weight;
Mw = weight average molecular weight;
polydispersity index = Mw/Mn;
the charge density is the number of sulphate groups per disaccharide unit;
ND = not identified As shown in Table 1, CS derived from land animals has similar molecular mass parameters (Mn and Mw), whereas it is different from that originating from fish species, which have higher molecular mass values. The terrestrial CS samples are also characterised by charge density (CD) values below 1.0, whereas the marine CS samples always have CD values exceeding 1.0. This characteristic is due to the different distribution of the sulphated disaccharides. Generally, disulphated disaccharides are found in trace amounts in terrestrial CS, and no polysulphated disaccharides (tri- and tetra-sulphates) are observed in natural CS.

The absence of tri- and tetra-sulphated disaccharides can easily be evidenced by analysis following digestion of the polysaccharide with chondroitinase ABC, a lytic enzyme specific for monosulphated disaccharides (Di-4S and Di-6S) and for unsulphated disaccharides (Di-0S), which are able to digest disulphated disaccharides but unable to hydrolyse the polysaccharide chain in correspondence with the polysulphated disaccharides. FACE (Fluorophore-Assisted Carbohydrate Electrophoresis) analysis of natural CS digested with chondroitinase ABC does not detect the electrophoresis bands characteristic of the partly undigested oligosaccharides which are found in synthetic or semisynthetic CS deriving from the prior art.

It is also well known that, due to biosynthesis processes, all natural CSs always show the simultaneous presence of monosulphated disaccharides at position 4 or 6 of GalNAc on the same polysaccharide chains (D'Arcy S M et al., Carbohydr Res. 1994 Mar. 4; 255:41-59. Hardingham T E et al., Carbohydr Res. 1994 Mar. 4; 255:241-54. Cheng F, et al., Glycobiology. 1992 December; 2(6):553-61. Chai W et al., Anal Biochem. 1996 May 15; 237(1):88-102. Zaia J et al., Anal Chem. 2001 Dec. 15; 73(24):6030-9. Desaire H et al., Anal Chem. 2001 Aug. 1; 73(15):3513-20).

Different activities have been reported for CS in relation to its molecular structure (Kimata K et al., Mol Cell Biochem 1, 211, 1963. Volpi N. Biomaterials 23, 3015, 2002. Volpi N, Tarugi P. Biochimie 81, 955, 1999. Volpi N. Biomaterials 20, 1359, 1999. Suzuki S et al., J Biol Chem 243, 7, 1968).

CS has anti-inflammatory activity, and is currently recommended in the treatment of osteoarthritis (OA) as a Symptomatic Slow-Acting Drug for OsteoArthritis (SYSA-DOA) in Europe, in particular for the treatment of osteoarthritis of the knee (Jordan K M et al., Ann Rheum Dis 62, 1145, 2003), hip (Jordan K M et al. Ann Rheum Dis 62, 1145, 2003) and hand (Zhang W et al., Ann Rheum Dis 66, 377, 2007) on the basis of clinical evidence and corresponding meta-analyses of numerous clinical trials. CS is also widely used as a nutraceutical in Europe and the USA, either alone or in combination with other ingredients (McAlindon T E et al., JAMA 283, 1469, 2000. Volpi N et al., Food Anal Meth 1, 195, 2008. Volpi N et al., Separation Sc 1, 22, 2009).

Commercial CS is obtained by extraction from animal tissue, such as bovine and porcine tissue (Fuentes E P et al., Acta Farm Bonaerense 17, 135, 1998), bird tissue (Luo X M et al., Poult Sci 81, 1086-1089, 2002) and fish cartilage (Sugahara K et al., Eur J Biochem 239, 871, 1996. Lignot B et al., J Biotechnol 103, 281, 2003).

The animal origin of commercial CS involves safety problems associated with transmissible infectious agents that cause diseases such as bovine spongiform encephalopathy (BSE), and restricts the possible sources available to meet the growing worldwide demand. These factors have stimulated research into alternative methods of producing CS.

Intensive efforts have been made to find a biotechnological method of producing CS, using a micro-organism as source of a precursor polysaccharide which has a structure partly similar to that of CS and conducting chemical sulphation to produce a CS similar to the natural one.

One example of this strategy is the production of biotechnological CS from capsular polysaccharide K4 of *E. coli* O5:K4:H4, as described in EP 1304338 B1. Said patent discloses a process wherein polysaccharide K4 produced in liquid cultures is extracted and purified, and then redissolved and subjected to acid hydrolysis to eliminate the fructose residues bonded to the GlcA residues of the polymer. The defructosylated polymer, identical to the unsulphated backbone of CS (CH), is then sulphated at position 4 or position 6 of the GalNAc residue according to two different chemical synthesis methods. Said patent also discloses a third method whereby a disulphated CS in both positions 4 and 6 is obtained. The CS described therein has a content of at least 70% of sulphated polysaccharides consisting of mono- and/or di-sulphated at position 4 and 6 of the GalNAc residue, position 2' of the GlcA residue being unsulphated, and has a molecular weight (Mw) of 6-25 kDa and a charge density (CD) of 0.7-2.0.

In EP 1304338 B1 the authors disclose and claim, depending on the synthesis strategy used, the possibility of:

a) synthesising CS 4S by selectively protecting position 6 of all the N-acetylgalactosamine (GalNAc) residues present, thus obtaining a polymer selectively sulphated only at position 4 of all the N-acetylgalactosamine (GalNAc) residues b) obtaining a polymer in which, similarly, the hydroxyl groups at position 6 of all the GalNAc residues are sulphated, suitably protecting the hydroxyl residues present at position 4.

In the process described in EP 1304338 B1, simultaneous sulphation therefore never takes place at positions 4 or 6 in the same chain, unlike the situation with natural CS.

A recent publication (Bedini E et al., Angew Chem Int Ed Engl. 2011 May 18) describes a process wherein the polysaccharide K4 produced is sulphated at position 4 and/or position 6 of the GalNAc residue in the same chain. However, the biotechnological CS described by Bedini et al. has a molecular weight similar to that of natural CS, namely around 17 kDa, leading to the low bioavailability typical of natural extracted products. Bedini et al. do not report any pharmacological characterisation of the product they obtained.

LIST OF FIGURES

FIG. 1 relates to natural chondroitin sulphate of bovine origin treated with chondroitinase C. Various oligosaccharides of different length demonstrating the presence of sulphate groups at position 4 or 6 of the GalNAc residue on the same polysaccharide chain are formed.

The chromatogram was obtained by gradient separation on a strong anion-exchange column (SAX-HPLC) and UV detection at 232 nm. The gradient was obtained by 50 mM NaCl up to 1.2 M NaCl from 0 to 60 minutes.

Figure 2:
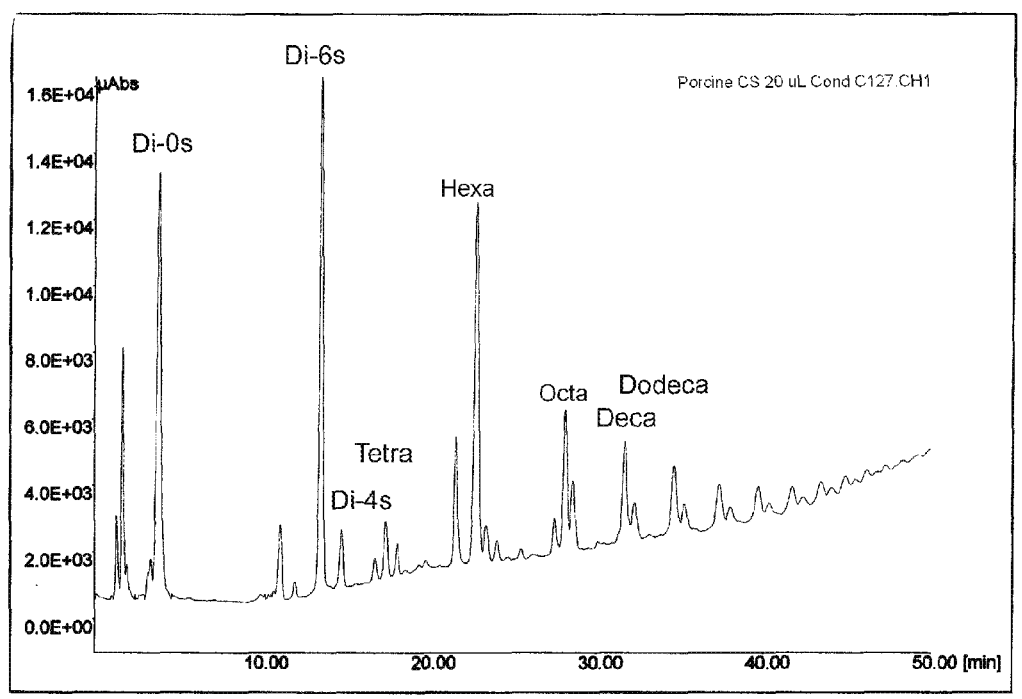

FIG. 2 relates to natural chondroitin sulphate of porcine origin treated with chondroitinase C. Various oligosaccharides of different length demonstrating the presence of sulphate groups at position 4 or 6 of the GalNAc residue on the same polysaccharide chain are formed.

The chromatogram was obtained by gradient separation on a strong anion-exchange column (SAX-HPLC) and UV detection at 232 nm.

Figure 3:
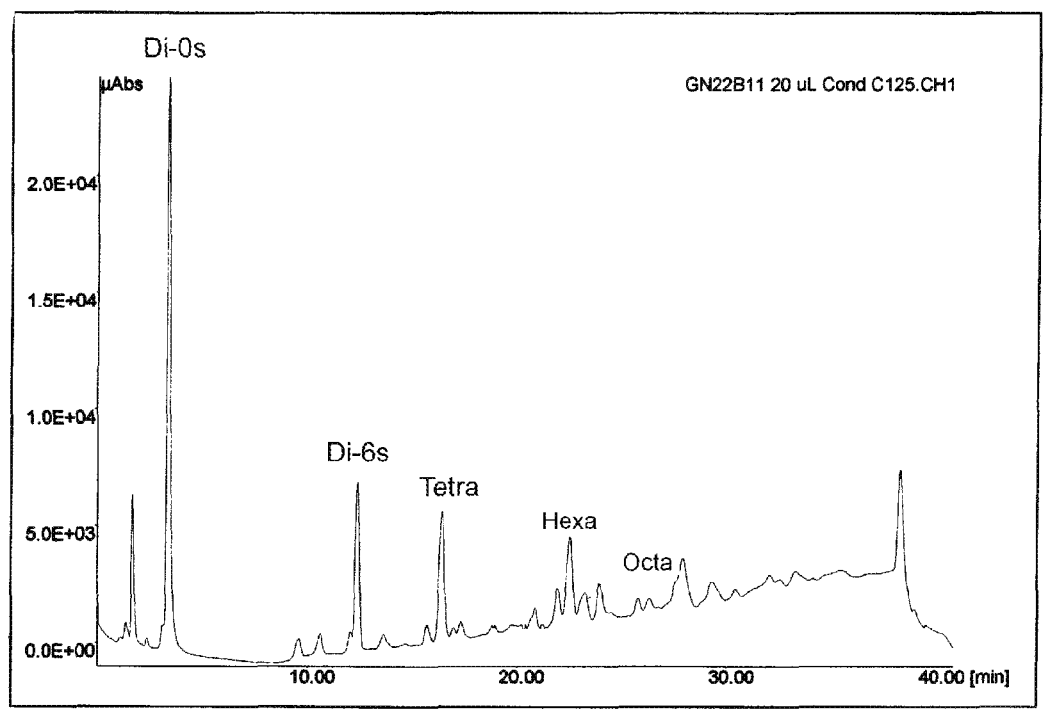

FIG. 3 relates to biotechnological chondroitin sulphate according to the present invention treated with chondroitinase C. Also for this polysaccharide various oligosaccharides of different length demonstrating the presence of sulphate groups at position 4 or 6 of the GalNAc residue on the same polysaccharide chain are formed.

The chromatogram was obtained by gradient separation on a strong anion-exchange column (SAX-HPLC) and UV detection at 232 nm.

DESCRIPTION OF THE INVENTION

The present invention describes a method for the production of CS following chemical sulphation starting from an unsulphated chondroitin backbone (CH), this CH being obtained by acid hydrolysis of a natural microbial polysaccharide i.1. (K4), or produced directly from a genetically modified *E. coli*, such as *E. coli* strain DSM23644, described in patent applications MI2010A001300 and MI2010A001264. The bacterial strain described therein carries a mutation that causes the inactivation of the KfoE gene for fructosylation of K4.

The CS obtained by the process according to the invention presents the characteristics of a natural CS with a titre exceeding 95% on the basis of the analytic methods described in the European Pharmacopoeia.

The CS obtained with the process according to the invention has an average molecular weight (Mw), measured by SEC, of 10-30 kDa, preferably 20-30 kDa, and presents a distribution of mono-sulphated groups ranging from 90% of 4-sulphate and 10% of 6-sulphate to 10% of 4-sulphate and 90% of 6-sulphate (Table 2).

TABLE 2

Characteristics of the CS described in this invention

| | |
|---|---|
| Mw (kDa) | 10-30 |
| Digestibility with chondroitinase ABC | >95% |
| Di-0S | <10% |
| Di-6S | 10-90% |
| Di-4S | 90-10% |
| Di-2,6diS | <5% |
| Di-4,6diS | <5% |
| Di-2,4diS | <5% |
| Di-triS | ND |
| Di-tetraS | ND |
| Titre (w/w) | >95% (o.d.b.)* |
| Charge density | 0.8-1.0 |
| Ratio 4S/6S | 0.1-9.0 |

*o.d.b.: on dry basis

The CS obtained with the process according to the invention contains a small amount (<10%) of unsulphated disaccharide and very low percentages (<5%) of disulphated disaccharides; trisulphated disaccharides cannot be identified.

The CS obtained with the process according to the invention is characterised by charge density values of 0.8-1.0.

In some forms of implementation of the present invention, the CS obtained shows a ratio between the sulphated disaccharide at position 4 (Di-4S) and the sulphated disaccharide at position 6 (Di-6S) of less than 1, whereas in other forms it shows a ratio between (4S) disaccharide and (6S) disaccharide greater than 1.

The process according to the present invention allows site-specific sulphation to be modulated to produce a CS with a specific 4S/6S ratio within the range specified above.

The present invention also relates to the production of chondroitin sulphate (CS) with low molecular weight (LMW-CS BIOTEC, 4,000-9,000 daltons) by chemical sulphation from a non-sulphated chondroitin backbone, which in turn is obtained by acid hydrolysis of the capsular polysaccharide K4 produced by *E. coli* strain O5:K4:H4, or directly produced from a genetically modified *E. coli*. The chondroitin sulphate with low molecular weight that is object of the invention is characterised by a molecular weight interval of 4,000-9,000 daltons, which is much less than that of chondroitin sulphates of natural origin, whether terrestrial, in particular of bovine, porcine or avian origin (14,000-26,000 daltons) or of marine origin, for example obtained from sharks, squid, rays or bony fish (generally >40,000 daltons). In view of these characteristics, the chondroitin sulphate according to the invention presents higher absorption after oral administration and therefore better bioavailability in humans than highly pure natural chondroitin sulphate or chondroitin sulphate produced by biotechnological/chemical processes. The chondroitin sulphate according to the invention possesses anti-inflammatory and anti-arthritic activity comparable with those of highly pure natural chondroitin sulphate. The chondroitin sulphate according to the invention is suitable for use in the treatment of inflammatory and osteoarthritic/arthritic processes.

The LMW-CS BIOTEC according to the invention has an average molecular weight, measured by SEC (Mw), of 4-9 kDa, and a distribution of mono-sulphated groups ranging from 90% 4-sulphate and 10% 6-sulphate to 10% 4-sulphate and 90% 6-sulphate. The characteristics of the low molecular weight CS according to the invention are substantially identical to those of the higher molecular weight derivatives reported in Table 2 above.

The LMW-CS BIOTEC according to the invention has a small quantity (<10%) of non-sulphated disaccharide and very low percentages (<5%) of disulphated disaccharides, while no trisulphated disaccharides are identifiable. LMW-CS BIOTEC is characterised by charge density values of 0.8-1.0, which are comparable with those of natural CS of terrestrial origin (see Table 1).

The process according to the invention also allows site-specific sulphation to be modulated in order to supply a CS with a specific 4S/6S ratio within the limits specified above, which are similar to those present in CS of natural origin.

The LMW-CS BIOTEC according to the invention is recognised and digested by chondroitinase ABC, a lytic enzyme which has the task of catabolising the natural CS in specific organisms, thus demonstrating that the polysaccharide chains of biotechnological LMW-CS have not undergone structural modifications liable to prejudice the specific, highly sensitive recognition of natural enzymes.

Finally, the LMW-CS BIOTEC digested with chondroitinase C, an endolyase that hydrolyses the polysaccharide in residues sulphated in position 6, but not in position 4, produces oligosaccharide sequences typical of the presence of Di-4S units alternating with Di-6S units on the same polysaccharide chain, as occurs in natural CS (FIGS. 1, 2 and 3). FIG. 1 in particular describes natural chondroitin sulphate of bovine origin treated with chondroitinase C. Oligosaccharides of different lengths can be seen which indicate the presence of sulphate groups in position 4 or 6 of the GalNAc residue on the same polysaccharide chain. The chromatogram was obtained by gradient separation on strong anion-exchange column (SAX-HPLC) and UV detection at 232 nm. The gradient was obtained with 50 mM NaCl to 1.2 M NaCl from 0 to 60 minutes;

FIG. 2 describes natural chondroitin sulphate of porcine origin treated with chondroitinase C. Oligosaccharides of different lengths can be seen which indicate the presence of sulphate groups in position 4 or 6 of the GalNAc residue on the same polysaccharide chain. The chromatogram was obtained by gradient separation on strong anion-exchange column (SAX-HPLC) and UV detection at 232 nm;

FIG. 3 describes the LMW-CS BIOTEC of the present invention, treated with chondroitinase C. Once again, oligosaccharides of different lengths are visible which indicate the presence of sulphate groups in position 4 or 6 of the GalNAc residue on the same polysaccharide chain.

The chromatogram was obtained by gradient separation on strong anion-exchange column (SAX-HPLC) and UV detection at 232 nm.

The LMW-CS BIOTEC according to the invention has been evaluated for oral absorption and bioavailability in humans by comparison with highly pure natural CS of bovine origin, the first standard of the European Pharmacopoeia.

This is particularly important because the presence of a bacterium able to biosynthesise a lytic enzyme specific for the breakdown of CS (and derivatives with low molecular weight) has been described in human but not animal bacterial flora (Ahn M Y, et al., Can J Microbiol 1998; 44: 423-9).

The oral absorption and bioavailability of LMW-CS BIOTEC have been evaluated in humans by known techniques.

The LMW-CS BIOTEC according to the invention was evaluated for possible anti-inflammatory activity using specific tests such as:

the ability to inhibit a proteolytic enzyme produced during inflammatory processes by the leucocytes, namely human leucocyte elastase (Kostoulas G. et al., Biol Chem 378, 1481, 1997; Volpi N. Chem Biol Interact 105, 157, 1997; Ying Q L et al., Am J Physiol. 272, L533, 1997); the ability to inhibit antichemotactic, phagocytic activity, lysozyme release and damage to the biological membrane by free radicals in human neutrophils (Matzner Y. et al., Thromb Haemost 52, 134, 1984; Ronca F, Palmieri L et al., Osteoarthritis Cartilage 6 Suppl A, 14, 1998).

These tests were conducted on the LMW-CS BIOTEC according to the invention by comparison with a reference compound, a highly pure natural CS of bovine origin which is the first standard of the European Pharmacopoeia.

The LMW-CS BIOTEC according to the invention was also evaluated for antiarthritic properties in an animal model, the "Adjuvant Arthritis (AA) model", which is widely recognised by the scientific community and has been published in numerous scientific papers. Once again, the results were compared with those previously obtained with the reference molecule: the European Pharmacopoeia standard, a highly pure natural CS of bovine origin (Volpi N. J Pharm Sci 96, 3168, 2007). In fact, animal models of OA and rheumatoid arthritis (AR) are useful tools for the study of these pathogenic processes. "Adjuvant Arthritis" (AA) is one of the most commonly used models. AA in the rat is an experimental model of polyarthritis which has been widely used to test numerous antiarthritic agents and medicaments before and after thorough clinical trials (Bendele A et al., Toxicol Pathol 27, 134, 1999; Rovensky J et al., Rheumatol Int. 31, 507, 2011; Bauerova K et al., Interdisc Toxicol 4, 101, 2011). Numerous studies have also been conducted wherein the data on animals obtained with the AA test were compared with the results in humans (Kannan K et al., Pathophysiology 12, 167, 2005).

Simultaneous monosulphation in position 4 or 6 of the polymer chain, purity and low molecular weight give the LMW-CS BIOTEC according to the invention greater oral absorption and better bioavailability.

One aspect of the present invention relates to the composition of the CS according to the invention and a carrier acceptable in the pharmaceutical or nutraceutical field. Said composition can be formulated in various solid forms, such as tablets, rigid capsules, soft gelatin capsules or powdered mixtures for drinks, or in liquid forms (solutions), preferably in the form of pharmaceutical or nutraceutical preparations for parenteral or oral administration. The composition can contain other active or inactive ingredients.

The composition can also, preferably, contain at least one of the following substances: gluco samine hydrochloride, gluco samine sulphate, N-acetyl glucosamine, hyaluronic acid, heparin, keratin, dermatin, methyl sulphonyl methane, folates and reduced folates, Group B vitamins, S-adenosyl-methionine (SAMe), ascorbic acid or manganese ascorbate. The composition can be administered to patients in effective quantities based on their needs.

For example, but without limiting its use, the CS or the composition described in the present invention can be administered in a quantity of between 100 and 3000 mg a daily, preferably between 1000 and 2000 mg a daily, and more preferably between 1250 and 1750 mg a daily, divided into two doses of approx. 600 mg or three doses of 400 mg a daily.

The present invention also relates to the use of the CS described, or a composition thereof, for the treatment or prevention of osteoarthritis or for the maintenance of musculoskeletal well-being as an ingredient of a medicament or nutritional supplement.

For example, the CS described or a composition thereof can be used to make a pharmaceutical preparation, dietary additive or nutritional supplement for the prevention and/or treatment of osteoarthritis of the hip, hand or knee and the main symptoms thereof (pain, joint swelling, inflammation), Alzheimer's disease, microbial infections, arteriosclerosis and osteoporosis, and as adjuvant in antitumoral treatment and tissue regeneration, including nerve tissue.

An advantageous characteristic of the process according to the invention is that the sulphation at position 4 or 6 of the GalNAc residue takes place simultaneously in the same polysaccharide chain, simulating the sulphation pattern observed in natural CS, unlike that obtained with the synthesis methods described to date. This aspect is confirmed by the data obtained with the use of two different enzymatic systems, namely chondroitinase ABC, which is able to digest units sulphated at position 6 and position 4 and unsulphated units, and chondroitinase C, an endolyase which is able to hydrolyse in correspondence with the residues sulphated at position 6 and unsulphated residues, but unable to perform similar lytic cleavage in correspondence with the residues sulphated at position 4. The products of digestion, obtained with chondroitinase ABC and with chondroitinase C alone, are analysed with HPLC chromatography techniques, as described by Joon-Soo Sim et al. (J. Chromatography B, 2005 vol. 818, 133-139), qualitatively and quantitatively indicating the presence of disaccharides Di-0S, Di-4S and Di-6S and any oligosaccharides not digested by the enzymes.

Analysis of the products of digestion with chondroitinase ABC demonstrates almost total digestion of the product with formation of the unsulphated disaccharide Di-0S, monosulphated disaccharides Di-4S and Di-6S, and traces of disulphated disaccharide Di-4,6S.

However, the same analysis conducted on the products of digestion with chondroitinase C clearly shows the presence of disaccharide sequences, and above all of oligosaccharide sequences, indicating the inability of the enzyme to break down the polysaccharide completely due to the presence on the same chains of GalNAc sulphated in 4. This is because when a sulphated residue is present in 4, the enzyme is unable to act, and consequently leaves oligosaccharide residues. Said residues are also clearly detected by chromatography and electrophoresis techniques, such as gel chromatography and capillary electrophoresis (CE), as shown, for example, in the chromatographic tracings in FIGS. 1, 2 and 3 relating to digestion with chondroitinase C of natural CS (bovine and porcine) and biotechnological CS obtained according to the present invention. They contain various oligosaccharides of different lengths wherein sulphate groups are present at position 4 or 6 of the GalNAc residue on the same polysaccharide chain.

All these properties give the CS obtained with the process according to the present invention the structure of a natural CS having the following characteristics:

a) all or nearly all the GalNAc residues are monosulphated at position 6 or 4;

b) depending on the synthesis conditions used, the ratio between residues 4S and 6S (4S/6S) is completely analogous to that found in CS of both terrestrial and fish origin.

Typically, the CS according to the present invention can be obtained using as starting substrate the capsular polysaccharide K4 naturally produced by *E. coli* strain O5:K4:H4 (EP 1304338 B1) or another polysaccharide having the structure of unsulphated chondroitin (CH).

In the first case, polysaccharide K4, obtained from a culture broth of *E. coli* strain O5:K4:H4, is defructosylated at the end of fermentation by thermoacid hydrolysis, and the chondroitin is purified in accordance with an adaptation of the methods described by Rodriguez and Jann (Eur. J. Biochem. 117, 117-124, FEBS 1988).

Alternatively, the starting polysaccharide is obtained, for example, from the culture of *E. coli* strain DSM23644 described in MI2010A001300 which, due to a mutation induced in the KfoE gene responsible for the fructosylation of K4, produces a polysaccharide identical to natural unsulphated CH. Defructosylation is not necessary in this case; however, the thermoacid hydrolysis step is maintained to eliminate some impurities, including the bacterial endotoxins that precipitate as a result of the treatment. The chondroitin (CH) is then purified by centrifugation, dialysis and spray drying.

Hydrolysis is conducted on the culture supernatant, separated from the biomass by continuous centrifugation. Partial hydrolysis and defructosylation of K4 is performed by incubation at 90-95° C. for 30-50 min at pH 2.8-3.0.

After the incubation period, the resulting suspension is cooled at a temperature below 40° C., preferably 20-30° C., to quench the hydrolysis reaction, and the pH is simultaneously adjusted to 4-4.5. The resulting suspension undergoes, in sequence, clarification by continuous centrifugation, ultrafiltration and finally, dialysis with water through a 30 kDa membrane.

The dialysed retentate (approx. 1/10th of the volume of the initial culture broth) is filtered and finally dried with a spray dryer to obtain a polysaccharide having the structure of CH, to be subjected to the sulphation process. The CH obtained has a titre of 80-90% on a dry basis (w/w), as determined by capillary electrophoresis (CE) or HPLC.

The CH thus obtained takes the form of the sodium salt, and in order to be sulphated needs to be converted to free acid or a salt thereof.

The sulphation process according to the present invention, which allows positions 4 or 6 of the GalNAc residue of the same polysaccharide chain to be monosulphated randomly, comprises the formation of an orthoester which simultaneously involves GalNAc positions 4 and 6 and its subsequent rearrangement to an ester which, surprisingly, can be modulated to release mainly the hydroxyl in 4 or in 6, thus allowing selective sulphation of those hydroxyls.

The process according to the invention comprises the following steps:

a) Conversion of the chondroitin sodium salt to free acid or, alternatively, to a salt thereof with a quaternary ammonium ion, such as tetramethyl-, tetraethyl- or tetrabutylammonium, or with pyridine. Tetrabutylammonium (TBA) salt is preferably used.

Alternatively, chondroitin (CH) in acid form is converted to its methyl ester after reaction in methanol and acetyl chloride.

b) Reaction of the chondroitin salt, or chondroitin methyl ester, with an orthoester of formula $RC(OR_1)_3$, wherein R is selected from hydrogen, methyl, ethyl or phenyl, and $R_1$ is selected from methyl or ethyl, in the presence of acid catalysis, thus obtaining a cyclic orthoester formed by the movement of two alkoxyls of the starting orthoester by alcohol functions 4 and 6 of the GalNAc residue. In the compound obtained in this step, all or nearly all the disaccharide units present possess a cyclic orthoester structure represented by formula I,

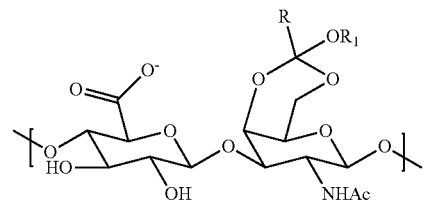

I wherein R, $R_1$ are as defined above.

Examples of orthoesters which can be used are trimethyl orthoacetate, triethyl orthoacetate, trimethyl orthoformate, triethyl orthoformate, trimethyl orthopropionate, triethyl orthopropionate or trimethyl orthobenzoate. Trimethyl orthoacetate or triethyl orthoacetate is preferably used. The use of trimethyl orthoacetate is particularly preferred.

An acid selected from camphorsulphonic acid, paratoluenesulphonic acid, methanesulphonic acid or a sulphone resin, preferably camphorsulphonic acid or a sulphonic resin, more preferably camphorsulphonic acid, is used as acid catalyst.

c) Protection of the alcohol groups at positions 2' and 3' of the GlcA residue by acylation with an anhydride of a carboxylic acid of formula $(R_2CO)_2O$, wherein $R_2$ is preferably selected from methyl, ethyl or propyl in the presence of pyridine or a tertiary organic base, such as triethylamine or triisopropylethylamine, and of catalytic quantities of 4-dimethylaminopyridine (DMAP), to give a product wherein the repeating disaccharide unit found in the chondroitin has a cyclic orthoester structure acylated in 2' and 3' which is represented by formula II

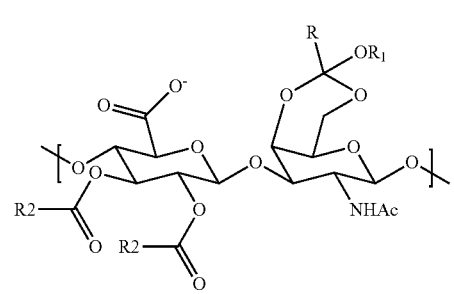

II wherein R, $R_1$ and $R_2$ are as defined above.

Acetic anhydride is preferably used.

d) Rearrangement from cyclic orthoester to ester, a reaction which is performed in a mixture of a water-soluble organic acid and water, or in water only. This rearrangement, which takes place randomly on the various GalNAc units of the polysaccharide sequence, can be modulated to promote the release of one or other hydroxyl (in 4 or 6 respectively), with simultaneous formation of the ester with the soluble organic acid used in the remaining position (6 or 4 respectively). The result is the formation, in the same polysaccharide chain, of two different disaccharide units, namely:

those with a structure wherein the hydroxyls at positions 6, 2' and 4' are acylated and the hydroxyl in 4 is free, said units being represented by formula IIIa;

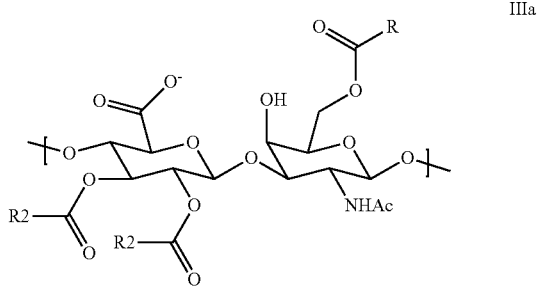

IIIa wherein R and $R_2$ are as defined above; or those with a structure wherein the hydroxyls at positions 4, 2' and 4' are acylated and the hydroxyl in 6 is free, said units being represented by formula IIIb

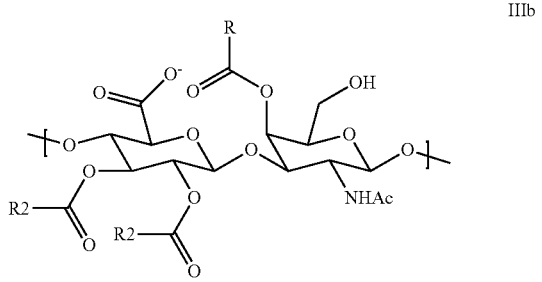

IIIb wherein R and $R_2$ are as defined above.

By conducting the reaction at a temperature of between 20 and 40° C., preferably at room temperature for a time of between 1 and 48 hours, preferably between 3 and 38 hours, and more preferably for 38 hours, a larger amount of compound having the free hydroxyl in 6 is surprisingly observed, whereas when the reaction is conducted at a temperature of between 40 and 70° C., preferably 60° C., for a time of between 1 and 48 hours, preferably between 3 and 38 hours, and more preferably for 18 hours, the product with the free hydroxyl at position 4 prevails. The water-soluble organic acid is selected from acetic, formic, propionic, tartaric citric acid or a cationic resin such as for example Sepra SCX 50 μm 65A, preferably acetic acid or propionic acid, and more preferably acetic acid.

d) This is followed by sulphation with pyridine sulphur trioxide in DMF according to the method already described in EP 1304338 B1, or with the DMF-sulphur trioxide complex, to obtain a CS which, according to the rearrangement conditions used and consequently the percentage of structures IIIa and IIIb present therein, will be simultaneously and variously sulphated at position 4 of disaccharide IIIa or position 6 of disaccharide IIIb. The sulphation reaction is followed by removal, by basic treatment, of the acyl groups present at positions 2' and 3' of the GlcA residue and positions 4 or 6 of the GalNAc residue, according to the procedures described in EP 1304338 B1, giving CS sodium salt which is partly sulphated in 4 and 6.

Some techniques used during the process lead to depolymerisation of the polysaccharide chain so as to produce a sulphated CS in position 4 or 6 of the GalNAc residue characterised by a low molecular weight (LMW).

Chondroitin can also be depolymerised at the orthoester rearrangement stage, using the acid as solvent or co-solvent of the reaction. The high concentration of acid at this stage leads to rupture of the polysaccharide chain, with consequent production of low molecular weight chains, in the 4-9 kD range.

The LMW-CS BIOTEC, 4,000-9,000 daltons, obtained by the process described, was evaluated for efficacy in an experimental animal arthritis model (Adjuvant Arthritis AA) in the rat, and the results were compared with those for pharmaceutical grade natural CS of extracted origin used in the same experimental model (Bauerova K. et al., Osteoarthritis Cartilage 2011, Epub ahead of print) after daily oral treatment with 900 mg/kg.

AA was induced by a single intradermal injection of *Mycobacterium butyricum* in incomplete Freund's adjuvant. The experiments comprised healthy animals, untreated arthritic animals and treated arthritic animals. Among the treated animals, one group of animals was subjected to pre-treatment consisting of administration of 900 mg/kg of LMW-CS BIOTEC a day for 14 days before arthritis was induced, continuing for 28 days after the induction of AA. Another group of animals was treated with 900 mg/kg of LMW-CS BIOTEC a day solely during the 28 days after the induction of AA.

The oedema that developed in the hind paw was significantly reduced in the pretreated animals. Pre-treatment with the LMW-CS BIOTEC according to the invention (900 mg/kg/day) significantly reduced oedema throughout the experiment compared with the untreated controls. Pre-treatment with LMW-CS BIOTEC also restores the body weight by approx. 8-15% compared with the untreated arthritic control.

The severity of the arthritis was quantified on the basis of increasing levels of swelling and periarticular erythema. 900 mg/kg/day of LMW-CS BIOTEC, administered as both pre-treatment and treatment, is significantly effective in reducing the arthritis score. Moreover, pre-treatment is effective throughout the subacute stage (from day 14 to day 28 after induction of AA), whereas the treatment is only effective in the medium-long term, in days 21-28 after induction of AA, not at the acute stage (the first 14 days after induction of AA).

Oxidative stress, a consequence of the chronic inflammatory processes that take place in arthritic/osteoarthritic processes, significantly increases in the animal model at both the acute and the subchronic stage. Increased oxidative stress induces high consumption of endogenous antioxidants in the plasma, and consequently causes a reduction in the plasma antioxidant capacity, measured as the total antioxidant status. Pre-treatment with LMW-CS BIOTEC is effective in correcting the total antioxidant status in the animal model, significantly reducing the consumption of endogenous antioxidants. The activity of γ-glutamyl transferase, which increases in correspondence with oxidative stress and is therefore considered to be a good marker for oxidative stress, measured in joint tissue homogenates, proved considerably greater in animals with experimentally induced polyarthritis, and considerably lower in the animals treated with LMW-CS BIOTEC, by comparison with the untreated animals.

Interleukin-1β (IL-1β and interleukin-6 (IL-6), pro-inflammatory cytokines, significantly increased in the animal model of experimentally induced arthritis, with a dramatic increase in IL-6 at the acute stage, presenting a level 10 times higher than the healthy controls. The therapeutic effect of LMW-CS BIOTEC was already evident from day 14, at the acute stage, reducing the IL-6 concentration by approx. 30-40% compared with the animals suffering from AA.

The basic marker for inflammatory proteins, namely C-reactive protein (CRP), has a very similar time profile to IL-6. The increase at the acute stage was approx. 7.5 times greater in the experimental arthritis model than the healthy controls. The effect of LMW-CS BIOTEC on CRP, like its effect on the IL-6 level, is observed at the acute stage, with a significant reduction in the plasma CRP concentration.

As regards the phagocytic activity and intracellular oxidative increase of the neutrophils, the differences observed between the healthy control and the control suffering from induced experimental AA were significant in the case of increased phagocytic activity. The administration of LMW-CS BIOTEC on a pre-treatment basis induced a significant reduction in phagocytosis and the oxidative burst.

The LMW-CS BIOTEC according to the invention significantly reduces the severity of the arthritic processes and the oxidative stress generated as a result of chronic inflammatory processes. Pre-treatment with LMW-CS BIOTEC is effective throughout the subacute stage, whereas treatment from day 1 of onset of AA is only effective during the chronic period. The effects are confirmed by an improvement in the total antioxidant status and activity of γ-glutamyl transferase. LMW-CS BIOTEC, administered as a pre-treatment, also reduces the production of pro-inflammatory cytokines, C-reactive protein in the plasma, phagocytic activity and the intracellular oxidative burst of the neutrophils. Finally, LMW-CS BIOTEC has proved effective in slowing the development of experimental arthritis/osteoarthritis at both the acute and the subchronic stage, and in reducing the markers of the disease, thus supporting its beneficial activity, on a par with that of the reference compound.

The invention will now be further illustrated by the following examples.

Example 1

Preparation of a Tetra-Alkyl Ammonium or Pyridinium Salt of Chondroitin

The CH sodium salt obtained after hydrolysis, purification and drying by the methods described above, starting from polysaccharide K4 or the polysaccharide obtained from fermentation of *E. Coli* strain DSM23644, is dissolved in an aqueous medium. After complete dissolution, the solution is introduced into a column packed with a cation-exchange resin, such as Amberjet 1200 H, Rohm and Haas, or equivalent.

The fractions eluted at pH 1.5-4.0, or preferably at pH 1.5-2.0, are collected, and an aqueous solution of an ion selected from tetramethyl-, tetraethyl- and tetrabutyl-ammonium or pyridinium is added until a pH of 6.0-8.0, or preferably 6.5-7.0, is obtained. The solution is then evaporated to complete dryness by freeze-drying or spray drying to obtain the corresponding salt.

Example 2

Protection of the Hydroxylated Functions (4 and 6) of the GalNAc Portion with Formation of the Corresponding Cyclic Methyl Orthoester CH (CH-cMOE)

The salt obtained from chondroitin, such as tetrabutyl ammonium (TBA) salt, is mixed with dimethylformamide (DMF) in a flask in the quantities of 5.2 g and 130 ml respectively. 8.49 g of trimethyl orthoacetate is dripped into the flask, followed by the addition of 300 mg of camphor-sulphonic acid, and the reaction mixture is maintained at 70° C. for 72 h. The reaction is then evaporated under vacuum to dryness, and further stove-dried at 40° C. for 20 h to obtain 6.1 g of chondroitin-MOE TBA in the form of a solid.

The analyses on the product of reaction were conducted to confirm that protection had taken place. The disappearance of the starting product and the appearance of a new product with a higher molecular weight (48 KDa) was established with SEC-HPLC. The analyses performed by digestion with chondroitinase ABC, an enzyme able to hydrolyse free but not protected CH, demonstrated that the unprotected percentage of starting CH molecules was under 15%.

Example 3

2',3' Acetylation of Chondroitin Cyclic Orthoester (2',3'Diacetyl CH-cMOE)

The chondroitin originating from the preceding step, protected as cyclic methyl orthoester (CH-cMOE) (4.79 g), is introduced into a reaction flask with 23.95 ml of acetonitrile, 15.69 ml of triethylamine (TEA), 6.21 ml of acetic anhydride and 78.96 mg of 4-dimethylaminopyridine (DMAP). After 2 hours' stirring at 25-26° C., 94 ml of di-isopropyl ether is added to obtain a viscous solid, which is then filtered through filter paper and stove-dried under vacuum at 45° C. for 24 h. The intermediate cyclic orthoester thus obtained has the appearance of a pink solid.

Example 4

Rearrangement from Cyclic Methyl Orthoester to Ester with Prevalent Formation of Acetate at Position 4, and with the Free Hydroxyl at Position 6 (See Figure IIIB)

The intermediate obtained from the preceding step (2.42 g) is introduced into a reaction flask, to which 18.8 ml of 96% acetic acid and 2.35 ml of demineralised water are added. The mixture is stirred for 38 h at room temperature, after which 100 ml of an 0.6 M solution of NaCl are added and the mixture is ultrafiltered through a 5 kDa membrane and dialysed, to recover a retentate with a pH of 3.32.

The solution is evaporated under vacuum at 45-50° C.; after further stove-drying overnight, 1.38 g of a product with the appearance of a vitreous solid are obtained.

Example 5

Rearrangement from Cyclic Methyl Orthoester to Ester with Prevalent Formation of the Acetate at Position 6, and with the Free Hydroxyl at Position 4 (See Figure IIIA)

2.42 g of intermediate cyclic orthoester obtained from the preceding step are introduced into a reaction flask with 14.52 ml of 96% acetic acid and 9.8 ml of demineralised water and heated to 60° C. for 17.5 h, 100 ml of 0.6 M NaCl are then added and the solution (pH 2.27) is ultrafiltered and dialysed to recover a retentate with a pH of 3.56.

The solution is evaporated under vacuum at 45-50° C., and after further stove-drying overnight, 1.12 g of a product with the appearance of a vitreous solid are obtained.

Example 6

Preparation of Chondroitin Sulphate with Sulphur Trioxide Pyridinium Complex

The intermediate obtained as described in example 4 (0.76 g) is introduced into a flask with 46.0 ml of DMF starring the mixture at 30° C. for 10 min. 0.72 g of sulphur trioxide pyridinium are added and when the starting material has dissolved (approx. 10 min), the solution is left under stirring at 30° C. for 1 h. A further 0.72 g of sulphur trioxide pyridinium are then added, followed by a further 0.72 g of sulphur trioxide pyridinium. The solution is stirred for a further hour at 30° C.

The reaction is quenched by pouring the mixture into 50 ml of 10% NaHCO$_3$ in water at room temperature (pH 7.81). After filtration the solution is evaporated under vacuum (10 mBar) to dryness, the residue redissolved with 150 ml of 0.6 M NaCl and, finally, the solution is ultrafiltered.

After 6 changes of volume the retentate has a pH of 9.22; the pH is adjusted to 6.7 with IN HCl and ultrafiltration continues, replacing the 0.6N NaCl solution with demineralised water.

The resulting solution is ultrafiltered again for 2 volumes, and then dialysed to a volume of 20 ml. The dialysed solution is concentrated to dryness under vacuum (10 mBar, 45° C.).

The product thus obtained (0.88 g) is dissolved with 34.0 ml of 0.2N soda (NaOH) and heated to 40° C. under stirring for 2 h. Finally, the solution is diluted with an 0.6M aqueous solution of sodium chloride, ultrafiltered through a 5 kDa membrane, and dialysed with demineralised water. The retentate is concentrated to dryness under vacuum (45° C., 10 mBar), to obtain 0.67 g of chondroitin sulphate. The end product, which has a molecular weight of 29 kDa, determined by HPLC-SEC, shows:

digestibility with chondroitinase ABC exceeding 95%;
a 4S/6S ratio of 18/82;
a total charge density value of approx. 0.9;
only partial digestibility with chondroitinase C, demonstrated by the presence of oligosaccharides due to the presence on the same polysaccharide chain of both 4-sulphated and 6-sulphated units, characteristic of the present invention.

Example 7

Preparation of Chondroitin Sulphate with Sulphur Trioxide Pyridinium Complex

The intermediate obtained as described in example 5 (1.12 g) is introduced into a flask with 67.2 ml of DMF, stirring the mixture at 50° C. for 10 min. 1.05 g of sulphur trioxide pyridinium are added, and when the starting material has dissolved (approx. 10 min), the solution is left under stirring at 50° C. for 1 h. A further 1.05 g of sulphur trioxide pyridinium are then added. The solution is stirred for a further hour at 50° C.

The reaction is quenched by pouring the mixture into 60 ml of 10% NaHCO$_3$ in water at room temperature (RT) (pH 7.81). After filtration the solution is evaporated under vacuum (10 mBar) to dryness, and the residue is redissolved with 30 ml of 0.6 M NaCl. Finally, the solution is ultrafiltered.

After 6 changes of volume the retentate has a pH of 9.22; the pH is adjusted to neutrality (7.5) with 1 N HCl and microfiltration continues, replacing the 0.6 N NaCl solution with demineralised water.

The resulting solution is ultrafiltered again for 2 volumes, and then dialysed to a volume of 20 ml. The dialysed solution is concentrated to dryness under vacuum (10 mBar, 45° C.), to obtain 1.53 g of product.

This residue is dissolved in 59.6 ml of 0.2 N soda (NaOH) and heated at 60° C. for 2 h. Finally, the solution is diluted with an 0.6M aqueous solution of sodium chloride, ultrafiltered through a 3 kDa membrane, and dialysed with demineralised water. The retentate is concentrated to dryness under vacuum (45° C., 10 mBar), to obtain 0.76 g of chondroitin sulphate.

The product thus obtained has a molecular weight of 15.4 kDa, determined by HPLC-SEC; digestibility with chondroitinase ABC exceeding 95%; a 4S/6S ratio of 82/18; and a total charge density value of approx. 1.09. The almost complete digestion obtained with chondroitinase ABC (over 95% of the product is broken down), together with reduced digestibility with chondroitinase C, which are characteristic of the present invention, demonstrate the existence of both 4-sulphated and 6-sulphated units on the same polysaccharide chain.

Over 95% digestibility with chondroitinase ABC also demonstrates the absence of polysulphated (tri- and tetrasulphated) disaccharides in the CS polysaccharide chain to which the present invention relates.

Example 8

Preparation of Chondroitin (CH) Methyl Ester 10.0 g of CH in acid form are added to a solution of 1.3 L of methanol and 14.43 g of acetyl chloride placed under stirring at room temperature for 2 hours in a 3 litre flask, and the suspension obtained is left under stirring for 20 hours.

When that time has elapsed, the suspension is filtered and the solid is washed with 100 ml of methanol (2×50 ml) and dried at 50° C. under vacuum to recover 9.4 g of dry solid.

The reaction is repeated a second time with the same procedure, and when the second period has elapsed, the suspension is cooled at between 0 and 5° C. for 60 minutes before filtration. The solid obtained is washed with cold methanol (0-5° C.) and stove-dried under vacuum for 3 hours at 50° C. to recover 6.3 g of solid.

Example 9

Protection of the Hydroxylated Functions (4 and 6) of the GalNAc Portion of CH Methyl Ester by Orthoester Formation 150 ml of dimethylformamide (DMF) and 6.0 g of the product obtained in the preceding step are introduced into a 500 ml flask with a calcium chloride valve and nitrogen flow. 20.06 g of trimethyl orthoacetate and 0.71 g of camphorsulphonic acid are then added. The solution obtained is heated at 50° C. (internal temperature) for 18 hours.

At the end of that period it is left to cool at RT and concentrated under vacuum to obtain 8.5 g of product.

Example 10

Acetylation of the 2',3' Hydroxyls of the Product Deriving from Example 9

8.0 g of the product obtained in the preceding step, 40 ml of DMF, 28.6 g of triethylamine, 17.15 g of acetic anhydride and 96 mg of dimethylaminopyridine are introduced into a 250 ml flask with a calcium chloride valve and nitrogen flow at room temperature.

The solution obtained is left under stirring for 3 hours; when that time has elapsed, 150 ml of isopropyl ether are added to the flask and an amorphous solid precipitates. The waters are eliminated by decanting and 100 ml of isopropyl ether are added to the solid and left under stirring for 1 hour. The solid is then filtered and washed with 50 ml of isopropyl ether and dried under vacuum at 40° C. to recover 8.52 g of product.

Example 11

Rearrangement of Orthoester Deriving from Example 10

7.0 g of the product obtained in the preceding step, 72.8 g of glacial acetic acid and 8.7 ml of water are introduced into a 250 ml flask to obtain a solution which is left under stirring at RT for 3 hours. The solution is then diluted to 150 ml with 0.6 M sodium chloride and the resulting solution is purified by ultrafiltration through a 5 KD membrane. After dialysis, the solution obtained is concentrated under vacuum and 6.7 g of solid product are recovered.

Example 12

Sulphation of Triacetyl Methyl Ester 670 mg of the product obtained in the preceding step are introduced into a 250 ml flask with nitrogen flow and calcium chloride valve with 40 ml of DMF.

630.44 g of sulphur trioxide pyridinium complex are added to the solution obtained and the resulting solution is heated at 50° C. (internal temperature) for 1 hour. 630.44 g of sulphur trioxide pyridinium complex are then added to the flask at the same temperature and again left under stirring for 1 hour.

When that time has elapsed, the solution is cooled to RT and 40 ml of 3% $NaHCO_3$ are added to the flask at the same temperature to produce a solution which is concentrated under vacuum to obtain 2.3 g of solid mixed with inorganic salts. The product obtained is diluted to 150 ml of 0.6 M sodium chloride and ultrafiltered through a 5 KDa membrane.

After dialysis, the solution obtained is concentrated under vacuum and 1.32 g of solid product are recovered.

Example 13

To Obtain Chondroitin Sulphate

The product obtained in the preceding step is introduced into a 100 ml flask with 33 ml of 0.2 M soda. The solution is heated at 40° C. (internal temperature) for 2 hours, after which it is cooled to RT and neutralised with 1M HCl.

The solution is diluted to 150 ml of 0.6 M sodium chloride and ultrafiltered through a 5 KDa membrane. After dialysis and concentration of the solution under vacuum, 350 mg of solid are obtained.

The product obtained in this example has a molecular weight of 11 KDa, a 4S/6S ratio of 47/53, and a charge density value of 0.9.

Example 14

Formation of Cyclic Orthoester on the Hydroxyl Functions in 4 and 6 of the GalNAc Portion, with Simultaneous Depolymerisation of the Polysaccharide Chain A suspension of chondroitin tetrabutylammonium salt, obtained as described above (4.07 g; 6.535 mmols), in dimethylformamide (101 ml), was maintained under stirring and under nitrogen flow at ambient temperature (20-25° C.). Trimethyl orthoacetate (9.03 ml, 71.89 mmols) and camphorsulphonic acid (1.82 g; 7.84 mmols) were added. The suspension was heated to 70° C. (internal temperature), and complete dissolution was observed after only a few minutes. The reaction was maintained under stirring at the same temperature for 18-20 h. The next day, the reaction was concentrated by removing the solvent by evaporation under vacuum, providing 13.67 g of the product in the form of a bright yellow rubbery residue.

The residual content of unprotected chondroitin after digestion is 4.6%. The presence of the orthoester is demonstrated by the corresponding signal in FTIR.

The product thus obtained was used in the subsequent steps as described above, until a LMW-CS BIOTEC sulphated in position 4 or 6 on the GalNAc residue was obtained.

Example 15

Opening of the Cyclic Orthoester of Chondroitin to Ester with Prevalent Formation of Acetate in Position 4 or 6 of the GalNAc Portion, and Simultaneous Depolymerisation of the Polysaccharide Chain Chondroitin orthoester (3.00 g), water (3.14 ml) and acetic acid (26.25 g; 437 mmols) were introduced into a 250 ml three-necked flask. The suspension obtained was heated for 36 h at ambient temperature (20-25° C.). Water was then added to make up the solution to a total volume of 100 ml. The solution thus obtained was ultrafiltered (5 KD membrane). The retentate collected was dialysed to a small volume (20 ml), and then concentrated until dry by evaporation under vacuum, providing 1.55 g of solid residue corresponding to the desired product (triacetyl chondroitin).

The product thus obtained was used in the subsequent steps as described above, until a LMW-CS BIOTEC sulphated in position 4 or 6 on the GalNAc residue was obtained.

Example 16

Induction of Arthritis (Adjuvant Arthritis, AA) in Rats, and Treatment with LMW-CS BIOTEC 40 male Lewis rats weighing between 150 and 190 g were randomised to four groups of 10 animals each, housed in polypropylene cages in a environment maintained at the temperature of 22±2° C., and fed on a standard laboratory diet with unlimited access to water.

The experimental groups were as follows:
1) An untreated healthy control group.
2) An untreated control group with adjuvant-induced arthritis (AA).
3) A group of arthritic rats treated orally with LMW-CS BIOTEC at the dose of 900 mg/day per kg of body weight for 28 days after induction of AA (days 0-28 of the experiment).
4) A group pretreated orally with LMW-CS BIOTEC at the dose of 900 mg/day per kg of body weight for 14 days preceding the induction of Articles of Association, and for the 28 days after induction of AA (days −14 to +28 of the experiment).

Arthritis was experimentally induced in the rats on day 0 by a single intradermal injection of 1 ml of a mixture consisting of *Mycobacterium butyricum* inactivated by heat in incomplete Freund's adjuvant.

The LMW-CS BIOTEC was dissolved in distilled water at the concentration of 20 mg/ml and administered orally as a single daily dose by gavage.

At the end of 28 days' treatment the rats were sacrificed under anaesthesia and the blood and tissues concerned were collected and analysed to evaluate the parameters observed in the study.

Example 17

Effects of LMW-CS BIOTEC on the Assessment of AA in Rats by Recording the Oedema Developed, Body Weight and the Arthritis Score The oedema that developed as a consequence of arthritis was measured by observing the increase in volume of the hind paw with a caliper suitable for the measurement. The measurements were performed before the induction of AA and on day 28 of the study.

The body weight of the rats was measured before induction of AA and at the end of the treatment (day 28). The effect of the treatment on this parameter was evaluated by comparing the various weight increases of the different groups during the treatment period.

The arthritis score was evaluated by attributing a score to the paw joint swelling and the extent of the periarticular erythema. The arthritis score or arthrogram was measured as the sum total of oedema (in ml, max. 8 points), plus the diameter of the forepaw (in mm, max 5 points), plus the diameter of the scab at the site of application of *Mycobacterium butyricum* measured parallel to the spinal column (in mm, max 5 points), for each animal.

Example 18

Effect of LMW-CS BIOTEC on the Activity of γ-Glutamyl Transferase as a Marker for Oxidative Stress Induced by AA Oxidative stress was evaluated by measuring the activity of γ-glutamyl transferase in homogenates of joint tissue taken from the rats at the end of the treatments with LMW-CS BIOTEC. γ-glutamyl transferase is considered to be a marker for oxidative stress.

The activity of the cell γ-glutamyl transferase was determined in homogenates of tissue taken from the hind paw, and evaluated by the Orlowski and Meister method (Orlowski M, Meister A. The gamma-glutamyl cycle: a possible transport system for amino acids. Proc Natl Acad Sci USA 1970; 67: 1248-1255) as modified by Ondrejickova et al. (Cardioscience 1993; 4: 225-230). The samples were homogenised in a buffer (2.6 mM $NaH_2PO_4$, 50 mM $Na_2HPO_4$, 15 mM EDTA, 68 mM NaCl, pH 8.1) in a 1:9 (w/v) solution with UltraTurax TP 18/10 (Janke & Kunkel, Germany) for 1 min at 0° C. The substrates, 8.7 mM of γ-glutamyl p-nitroanilide and 44 mM of methionine, were added to 65% of isopropyl alcohol at final concentrations of 2.5 mM and 12.6 mM respectively. After incubation for 60 min at 37° C., the reaction was stopped by adding 2.3 ml of cold methanol, and the test tubes were centrifuged for 20 min at 5000 rpm. The absorbance of the supernatant was measured with a Specord 40 spectrophotometer (Jena, Germany) in 0.5 cm cuvettes at 406 nm Reaction mixtures in the absence of substrate or acceptor were used as reference samples.

Example 19

Effect of LMW-CS BIOTEC on the Inflammatory State Induced by AA by Evaluating the Levels of Pro-Inflammatory Cytokines (I-1, IL-6) and C-Reactive Protein (CRP) in the Plasma Blood samples were drawn from the rats at the end of the experiment and placed in test tubes containing heparin as anticoagulant; the plasma was separated from the corpuscular part consisting of blood cells by centrifugation, and the inflammatory cytokines (IL-1, IL-6) were assayed with the ELISA technique using specific commercial kits.

C-reactive protein was assayed in the rat plasma with an ELISA kit (Immunology Consultant Laboratories, Inc., ICL). The reaction of the biotin-conjugated secondary antibody with anti-rat C-reactive protein antibodies was evaluated by means of the activity of streptavidin-horseradish peroxidase (HRP). The reaction of methyl-benzidine with HRP bonded to immune complexes was then measured at 450 nm using a Labsystems Multiskan RC microplate reader. The results were calculated using the standard calibration curve in accordance with the ELISA kit instructions.

Example 20

Effect of LMW-CS BIOTEC on Phagocytic Activity and on the Neutrophil Oxidative Burst Induced by AA The neutrophil population was extracted from the blood of the rats at the end of the evaluation of their phagocytic activity and oxidative burst. The measurement of phagocytosis, namely ingestion of bacteria, was performed under controlled conditions using opsonised *Staphylococcus aureus* labelled with fluorescein (SPA-FITC) (Invitrogen Molecular Probes, USA). Aliquots of peripheral blood in lithium-heparin were then incubated with hydroethidine (Invitrogen molecular probes, USA) (15.75 mg in 5 ml of dimethylformamide, Merck, Germany) for 15 minutes at 37° C. After treatment with SPA-FITC for 15 minutes at 37° C., the reaction was interrupted by placing the test tubes in ice. The subsequent lysis of the erythrocytes was performed for 15 min with a lysis solution consisting of cold ammonium chloride/potassium chloride (200 ml deionised water, 1.658 g $NH_4Cl$, 0.2 g $KHCO_3$ and 7.4 mg $Na_2EDTA$, pH 7.2-7.4). The average percentage of phagocyte cells represents the percentage of granulocytes which ingested at least one particle of SPA-FITC, and the average percentage of the respiratory burst represents the percentage of granulocytes labelled with ethidium.

The invention claimed is:
1. Process for the preparation of chondroitin sulphate sodium salt in which all the N-acetyl-D-galactosamine units in the same polysaccharide chain are monosulphated either randomly or at the 4- or 6-position, said process comprising the following steps:
   a. transforming chondroitin sodium salt into its free acid or a salt thereof with a quaternary ammonium cation selected from tetramethylammonium, tetraethylammonium or tetrabutyl-ammonium, or into the pyridinium salt or the methyl ester;
   b. reacting the compound obtained in step a) with an orthoester of formula $RC(OR_1)_3$, in which R is selected from hydrogen, methyl, ethyl or phenyl and $R_1$ is selected from methyl or ethyl, in the presence of acid catalysis, to give a compound in which the repeating disaccharide unit present in chondroitin has the formula I

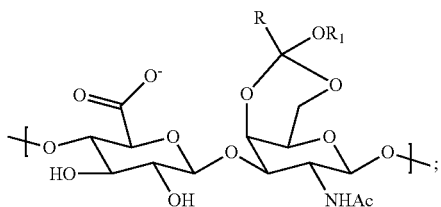

in which R and R1 are as defined above;
   c. protecting the hydroxy groups at the 2'- and 3'-positions of the glucuronic acid units of the compound obtained in the previous step by reaction with an anhydride of formula $(R_2CO)_2O$ in which $R_2$ is selected from methyl, ethyl or propyl, in the presence of pyridine or an organic tertiary base selected from triethylamine or triisopropylamine and of 4-dimethylaminopyridine (DMAP), to give a compound in which the repeating disaccharide unit present in chondroitin has the formula II

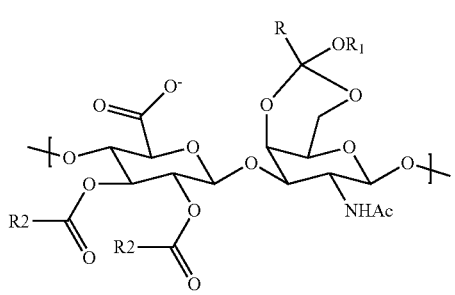

in which R, $R_1$ and $R_2$ are as defined above;
   d. rearranging the orthoester functionality present in the product obtained in step c) with an organic water-soluble acid to give an ester derivative in which the repeating GalNAc units in the polysaccharide consist of triacyl derivatives having formula IIIa or IIIb

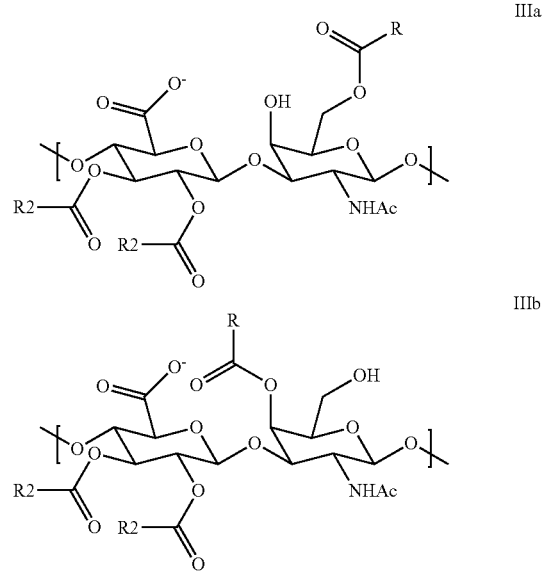

in which R and $R_2$ are as defined above;
   e. mono-sulphating the compound obtained in step d) followed by removal of the O-acyl groups present in compounds IIIa and IIIb obtained in the previous step.

2. The process of claim 1 wherein the chondroitin sodium salt of step a) is obtained starting either from the capsular polysaccharide K4 produced by a culture broth of *E. Coli* strain O5:K4:H4, or from the polysaccharide produced by a culture broth of *E. Coli* strain DSM23644.

3. The process of claim 1 wherein step b) is carried out with an orthoester selected from trimethyl orthoacetate, triethyl orthoacetate, trimethyl orthoformate, triethyl orthoformate, trimethyl orthopropionate, triethyl orthopropionate or trimethyl orthobenzoate.

4. The process of claim 1 wherein the acid catalysis of step b) is carried out with an acid selected from camphorsulphonic acid, para-toluenesulphonic acid, methanesulphonic acid or a sulphone resin.

5. The process of claim 1 wherein step c) is effected with acetic anhydride.

6. The process of claim 1 wherein step d) is effected from about 20° C. to about 40° C.

7. The process of claim 1 wherein step d) is effected from about 40° C. to about 70° C.

8. The process of claim 1 wherein step d) is effected in a water/organic water-soluble acid mixture or in water alone.

9. The process of claim 8, wherein the organic acid is selected from acetic, formic, propionic, tartaric, citric acid or a propionic resin.

10. The process of claim 1 wherein the obtained chondroitin sulphate sodium salt has an average molecular weight (Mw) of 10-30 kDa.

11. The process of claim 10 wherein chondroitin sulphate sodium salt has a distribution of monosulphate groups whose ratio ranges from 90/10 4S/6S to 10/90 4S/6S.

12. The process of claim 1 wherein the ratio between the sulphated N-acetyl-D-galactosamine units at the 4-position and the 6-position in the obtained chondroitin sulphate sodium salt is lower than 1.

13. The process of claim 1 wherein the ratio between the sulphated N-acetyl-D-galactosamine units at the 4-position and the 6-position in the obtained chondroitin sulphate sodium salt is higher than 1.

* * * * *